United States Patent [19]

Flanagan et al.

[11] 4,112,302
[45] Sep. 5, 1978

[54] GAS MONITOR

[75] Inventors: Brian S. Flanagan, San Diego; Phillip L. Turner, Del Mar; Richard D. Broce, Vista; Peter L. Lagus, Olivenhain, all of Calif.

[73] Assignee: Systems, Science and Software, La Jolla, Calif.

[21] Appl. No.: 773,605

[22] Filed: Mar. 2, 1977

[51] Int. Cl.² ............................................. G01T 1/18
[52] U.S. Cl. ............................................. 250/381
[58] Field of Search ...................................... 250/381

[56] References Cited
U.S. PATENT DOCUMENTS

| 3,176,135 | 3/1965 | Lovelock | 250/381 |
| 3,714,421 | 1/1973 | Josias et al. | 250/381 |

Primary Examiner—Davis L. Willis
Attorney, Agent, or Firm—Fitch, Even, Tabin & Luedeka

[57] ABSTRACT

A gas monitor comprising means for detecting changes in electron flow between two electrodes caused by absorption of the electrons by an electron capture gas flowing between the electrodes. A carrier gas is supplied to the detecting means at a predetermined velocity. A sample of the gas to be measured is added to the carrier gas by a valve means at a predetermined time which gas sample contains a trace of a first type of electron capture gas. The carrier gas together with any gas sample flows through a column means which slows down the velocity of any other type of electron capture gas in the sample with respect to the velocity of the first type of electron capture gas. The gas then passes through the detector wherein the electron capture gas causes a decrease in the electron flow between the electrodes. Means are provided for measuring the maximum decrease in the electron flow caused by the first type of electron capture gas and means are coupled to the measuring means for indicating the maximum decrease.

9 Claims, 1 Drawing Figure

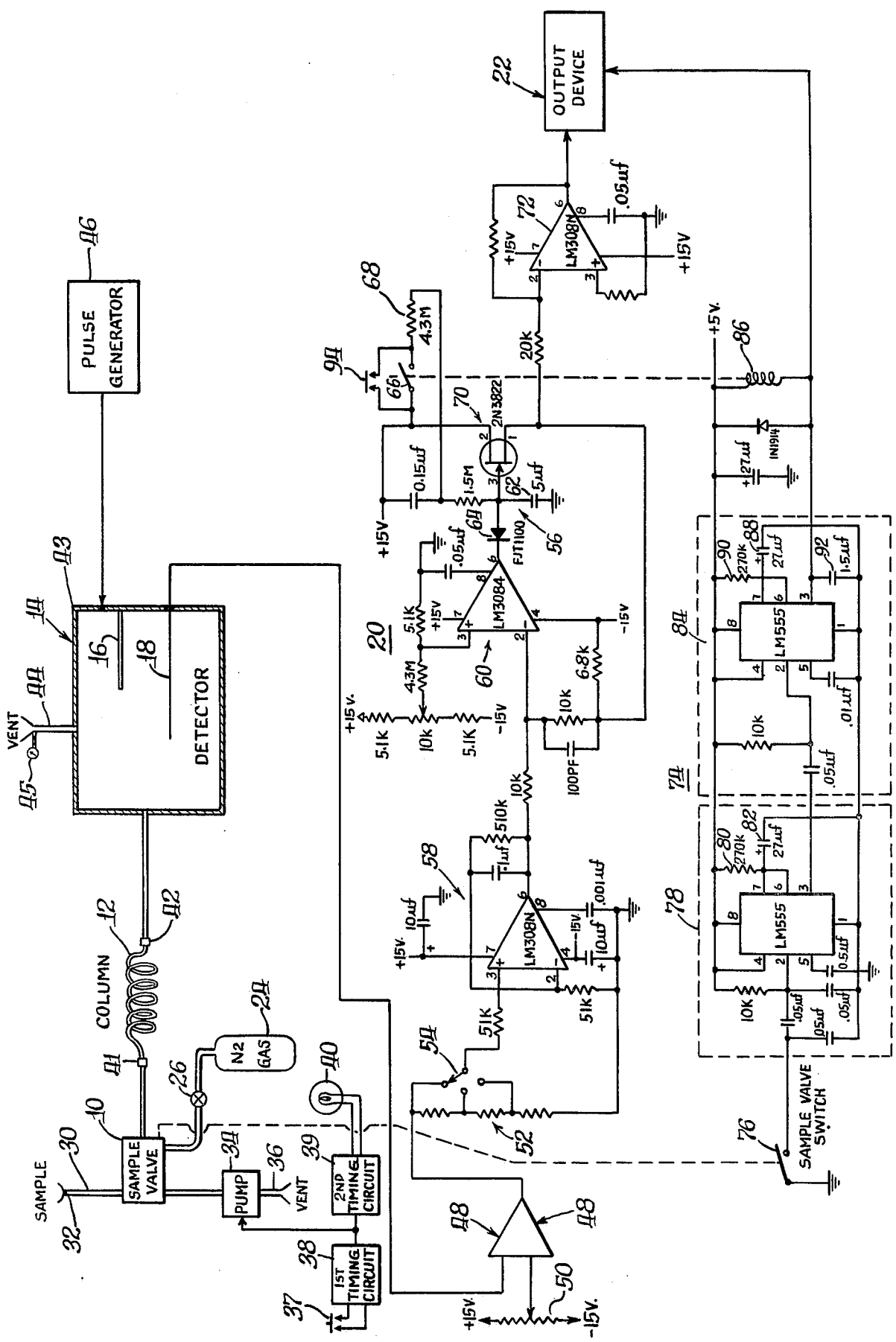

GAS MONITOR

The present invention relates to gas monitors and, more particularly, to a tracer gas monitor utilizing gas chromatography or separation.

Prior art tracer gas monitors have utilized gas chromatography to selectively separate the tracer gas from the remainder of the gas sample. The concentration of the tracer was determined by an electron capture detector. Such gas monitors were employed to perform tracer gas studies of fossil fuel power plant plumes but were difficult to use, limited in application, and required trained technicians for operation.

It is an object of the present invention to provide a tracer gas monitor, utilizing gas chromatography, which is economical and versatile and can be used by relatively untrained technicians.

This and other objects of the invention will become more apparent by reference to the following description and accompanying drawing which shows a schematic diagram of a tracer gas monitor in accordance with the present invention.

Generally, as shown in the drawing, the gas monitor, in accordance with the present invention, is designed to sample and log an electron capture tracer gas. A sample of the gas to be tested, which gas contains the tracer gas, is injected by a valve means 10 into a flow of carrier gas. The carrier gas with the gas sample flows through a molecular sieve column 12 which separates the tracer gas from any other electron capture gas in the sample. The output of the column 12 flows to an electron capture detector 14 wherein the tracer gas absorbs the electrons passing between two electrodes 16 and 18 disposed within the detector and thereby reduces the electron flow. The decrease in the electron flow is measured by a sample and hold circuit means 20 which is activated at a time prior to the separated tracer gas flowing between the electrodes 16 and 18 and is deactivated prior to the arrival of any other electron absorbing gas. The peak reduction in electron flow is read by an output device 22 which is connected to the output of the sample and hold circuit 20. The concentration of the tracer gas may then be determined by reference to a calibration chart.

More particularly, as shown in the drawing, a source or bottle 24 of an inert carrier gas, such as nitrogen is connected by tubing to a flow adjustment valve 26 which, in turn, is connected by tubing to the sample valve 10 that injects gas samples into the carrier gas. The valve 10 may be a conventional electrically operated, micro-volume sample valve with a loop volume of 2 ml, such as that made by Carle.

The gas sample, which in the preferred embodiment is atmospheric gas containing the tracer gas, is supplied to the sample valve by a sample tube 30 connected by one end to the sample valve 10. The entry or free end of the sample tube 30 is provided with a septum 32 which prevents reverse flow of the gas sample. The gas sample may be introduced into the sample tube 30 by syringe injection of a sample through the septum 32 or by drawing the sample gas into the sample tube 30, subsequent to removal of septum 32, by means of an electrically operated gas pump 34 having its inlet connected to the valve 10 and its outlet connected to a vent 36. The sample pump acts to draw a gas sample through the monitor tubing and is located at the physical end of the sampling train. This allows one to use a pump and still not contaminate a gas sample which is to be analyzed by accumulation of contaminants or tracer gas within the pump itself. A pump located forward of the detector, column or sample valve in the sample train can collect concentrations of contaminants or tracer gas and outgas them at some later time thereby possibly affecting the apparent concentration of the gas being analyzed.

The pump is energized for a predetermined time by manually closing a switch 37 which activates a first timing circuit 38 the output of which is connected to the pump 34. When the timing circuit 38 times out, it turns off the pump 34 and activates a second timer 39, the output of which actuates for a predetermined time a ready lamp 40 indicating that a gas sample is present in the sample valve 10 and may be injected into the carrier gas stream. When using the pump 34 for sampling it is necessary to inject the sample during the time this lamp 40 is lit. Otherwise the sample concentration may be diluted by diffusion because with the septum 32 removed the sample valve input line 30 is open to outside air. In the case of syringe sampling this light 40 is not lit since the septum 32 acts to seal the sample valve input line and prevent back diffusion of the gas sample to be analyzed. The gas sample in the sample valve 10 is injected into the carrier gas by actuation of the sample valve 10.

The sample gas contains the electron capture tracer gas which preferably is sulfur hexafluoride because it is transported and dispersed as other atmospheric gases. Also, it is non-toxic chemically inert, odorless, tasteless, and can be detected at very low concentrations (e.g., $10^{-12}$ parts sulfur hexafluoride per part of air). In certain applications other halogenated tracer gases may be used.

The carrier gas flows through the sample valve 10 and through tubing to the input of the molecular sieve column 12. The column 12 separates the various gaseous components of gas passing therethrough by selectively slowing some gases relative to others, and thus places the distinct components in a gas passing therethrough in a definite order. The illustrated molecular sieve column 12 allows the sulfur hexafluoride tracer gas to pass through before the oxygen within the sample gas thereby facilitating the detection of low level signals which might be lost in the tail of a strong oxygen peak.

In the illustrated embodiment, the molecular sieve column 12 is a coil of tubing about 1 meter long having particles of synthetic zeolite, which possess 5A sized pores, disposed therein. The synthetic zeolite is activated by heating the tube with the zeolite therein to 200° F for 8 hours in a nitrogen atmosphere. The column once activated should be maintained in a dry nitrogen environment at all times. To permit this, the input and output of the column are provided with quick disconnect type fittings 41 and 42, such as conventional Swagelok fittings with high temperature seals, that seal the column and prevent exposure to air. High temperature seals are required to allow reconditioning of the column at elevated temperatures.

After passing through the column 12 the carrier gas and any accompanying gas sample flow to the detector 14. The detector 14 includes an electrically conductive housing 43, a central electrode 18, and a source of ionizing electrons 16 preferably a beta source such as a tritiated titanium foil having a source strength of about 300 mCi. The central electrode 18 is encased within and is electrically separated from the electrically conductive housing 43. A vent for the gas in the housing 43 is provided by a tube 44 connected to the housing 43 and the flow of gas through the system is monitored by a gas flow meter 45 connected to the outlet of the tube 44. The housing 43 is repeatedly pulsed to a negative voltage (eg., −30 volts) by a pulse generator 46, described hereinafter, connected to the housing 43. The ionizing source 16 produces energetic electrons by means of radioactive decay. These energetic electrons in turn ionize any gas present between the conductive housing 43 and the electrode 18 producing less energetic secondary electrons. Repeated pulsing of the conductive housing 43 drives the secondary electrons toward the electrode 18 where they are collected and produce a current which is measured by an electrometer circuit 48 described hereinafter. Any electron capture gas flowing between the electrodes 16 and the conductive housing 43 absorbs electrons and thereby reduces the electron flow or current in proportion to the concentration of the electron capture gas.

In the illustrated embodiment, the electrometer circuit 48 includes a conventional operational amplifier having one input connected to the electrode 18 and the other input connected to the moveable tap of a zero adjustment potentiometer 50.

In the illustrated embodiment, the pulse generator 46 provides a series of negative pulses to the housing 43 of the detector 14, the pulses being at a repetition rate and having a pulse width such as to produce an average current in the detector which permits operation of the detector over its linear region of sensitivity. The position of the linear region of sensitivity of the detector varies with the flow rate of the carrier gas, the concentration of the electron capture gas in the gas sample, and the spacing of the electrodes. For an electrode spacing of about 5/32 of an inch, a carrier gas flow of 0.1 SCFH, to measure a $10^{-9}$ to $10^{-12}$ parts of sulfur hexafluoride in air over a linear region of sensitivity, a pulse rate of 130 microseconds and a pulse width of 1 to 1½ microseconds is employed. To measure $10^{-6}$ parts of sulfur hexafluoride in air, the repetition rate should be increased to about 15 microseconds.

The pulse generator 46 employs conventional circuitry and may include a crystal oscillator (not shown) operating at 1.0 megahertz, the output of which is connected to a divider circuit (not shown) which divides the output by about eight. The divider circuit is connected in turn to a pulse forming and drive circuit (not shown), the output of which is connected to the detector 14.

The output of the electrometer 48 is connected to a range switch 52, the moveable contact 54 of which is connected to the sample and hold circuit means 20 which measures and holds the maximum decrease or peak in the electron flow caused by the electron capturing tracer gas while excluding the peak caused by any other electron capture gas which may be contained in the gas sample. In the illustrated embodiment, this means 20 includes a peak read and hold circuit 56 coupled to the moveable contact 54 through a pair of amplifiers 58 and 60, which are conventional operational amplifiers, connected so as to cause a decrease in the dc output of the second amplifier 60 when there is a decrease in the electron flow through the detector. The peak read and hold circuit 56 includes a capacitor 62 having one end grounded and the other end coupled through a unidirectional device 64, such as a diode, to the output of the second amplifier 60. The unidirectional device 64 is oriented so that the capacitor 62 is discharged only when the output of the amplifier 60 is below the voltage across the capacitor 62, whereby the voltage across the capacitor 62 indicates the maximum decrease in the electron flow. The capacitor 62 is charged to its fully charged condition (i.e., normalized or zeroed) by coupling a positive voltage thereto through a closed normally open relay contact 66 and a series resistor 68.

The voltage developed across the capacitor 62 is amplified by a high input impedance amplifier 70, such as a conventional FET amplifier, and a second amplifier 72, such as a conventional operational amplifier. The output of the second amplifier is coupled to the input of the output device 22, which is a digital display such as a conventional 3 digit light emitting diode (LED) type having internal BCD conversion.

So that only the peak created by the electron capture tracer gas is measured by the peak read and hold circuit 56, a peak window circuit 74 controls the sampling time of that circuit 56 by maintaining the capacitor 62 in its normalized condition from the time the gas sample is injected into the carrier gas until a time just prior to the arrival of the tracer gas at the detector 14 and then returning it to its normalized condition just after the tracer gas passes beyond the detector 14. At the same time, the peak window circuit 74 provides a hold signal to the LED display 22 to thereby hold the last reading of the LED display 22. In the illustrated embodiment, the peak window circuit 74 is activated by a normally open sample switch 76 which is closed by actuation of the sample valve 10, as for example by positioning the sample switch 76 so that it is mechanically closed by the stem of the sample valve 10. The closing of the sample switch 76 provides a pulse to the trigger of a first timer 78, which may comprise a conventional linear integrated timing circuit, the timing of which is determined by a resistor 80 and capacitor 82. The resistor 80 and capacitor are selected so that it times out at a time slightly less than the required for the electron capture tracer gas to pass from the sample valve 10, through the column 12 to the detector 14. The output of the first timer 78 is applied to the trigger of a second timer 84 which also may be a conventional linear integrated timing circuit. Until the trigger signal is applied to the second timer 84, its output is low and this maintains a relay coil 86 connected to the output energized and thus its contact 66 closed to thereby maintain the capacitor 62 in its normalized condition. After the second timer 84 is triggered, its output is high thereby dropping out the relay 86 which, in turn, allows the capacitor 62 to sense current changes. The timing of the second timer 84 is selected, by selecting the values of the capacitor 88 and resistor 90, so that it times out at a time just after the electron capture tracer gas passes beyond the electrodes 14 and 16 in the detector. After the second timer 84 times out, the output is rendered low again thereby picking up the relay 86, closing its normally open contact 66 and again normalizing the capacitor 62. At the same time, the output of the second timer 84 provides a hold command to the LED display 22.

The effect of the relay coil 86 and its associated contact 66 is to suppress any spurious non-tracer gas related electrical signal from influencing the reading on the LED display 22 by not allowing the capacitor 62 to lose charge except when the timing window is open. Such spurious signals may be generated by: (i) momentary interruption of carrier gas flow resulting from actuation of the sample valve 10; (ii) presence later in time of other electron capture gas, notably oxygen; and (iii) electrical noise generated by AC or DC motors operated nearby, e.g. electric drills.

A manually operated, normally open zero switch 94 is connected in parallel with the relay contact 66 to permit zero adjustment of the monitor. In this connection, the zero switch 94 is closed and the zero adjust potentiometer 50 is adjusted to zero the digital display 22.

In operation, the nitrogen supply 24 is adjusted to a flow rate of 0.1 SCFH and the digital display is zeroed. A gas sample is then introduced into the system by inserting a syringe through the septum 32 or by actuating the pump 34 by pressing the pump switch 37. With the septum removed, if the pump switch is pressed, the gas sample is drawn into the system through the sample tube 30 for a predetermined time after which the pump is turned off and the ready indicator 40 lights. The sample valve 10 is actuated to inject the gas sample into the carrier gas stream. The actuation of the sample valve 10 initiates the timing of the first timer 78 in the peak window circuit 74. While this first timer is in operation, the carrier gas and the gas sample gas flow through the column 12 wherein the electron capture tracer gas is allowed to pass through while any other electron capture gas in the gas sample is retarded. The carrier gas and the gas sample then flow to the detector 14 wherein the electron capture tracer gas decreases the electron flow in the detector. In the meantime, the first timer 78 has timed out thereby permitting the peak read and hold circuit to read the change in the electron flow caused by the electron capture tracer gas. The peak value of the change in the electron flow caused by the electron capture tracer gas is stored in the capacitor 62 and this peak value is read on the LED display 22. After the electron capture tracer gas flows through the detector, the second timer 84 in the peak window circuit times out to close the window and to hold the numbers in the LED display 22. The tracer gas concentration in the air can be then determined by a calibration curve.

The disclosed gas monitor permits studies of industrial and power plant emission plumes, as well as for general air flow ventilation type endeavors. The operation of the monitor is relatively simple to operate whereby highly skilled technical personnel are not required to oversee operation of the monitor, yet reliable data can be obtained with a minimum of time and effort.

Various changes and modifications may be made in the above-described gas monitor without deviating from the spirit or scope of the present invention. Various features of the present invention are set forth in the following claims.

What is claimed is:

1. A gas monitor comprising means for detecting changes in electron flow between two electrodes caused by absorption of the electrons by an electron capture gas flowing between said electrodes, means for supplying a carrier gas to said detecting means at a predetermined velocity, valve means for adding a sample of gas to said carrier gas at a first predetermined time, said sample gas containing a trace of a first type of electron capture gas, column means connected between said adding means and said detecting means for selectively slowing down the velocity of any other type of electron capture gas in said sample with respect to the velocity of the first type of electron capture gas, means coupled to said detector for measuring the maximum decrease in the electron flow caused by said first type of electron capture gas, and means coupled to said measuring means for indicating said maximum decrease.

2. A gas monitor in accordance with claim 1 wherein said first type of gas is sulfur hexafluoride.

3. A gas monitor in accordance with claim 1 wherein said detecting means includes a tritium foil as a source of ionizing electrons.

4. A gas monitor in accordance with claim 1 wherein the column means is provided with a quick disconnect type fitting at its input and output so as to permit the column to be maintained in a dry nitrogen environment after it is activated for use in the gas monitor.

5. A gas monitor in accordance with claim 1 wherein a pump is connected to said valve means so as to draw said sample of gas into said valve means when actuated, first timing means is connected to said pump for actuating said pump for a first predetermined time interval, and second timing means is provided which is actuated by said first timing means after said first predetermined time interval and which lights an indicating device for a second predetermined time during which said valve means should be actuated to prevent dilution of the concentration of the sample.

6. A gas monitor comprising means for detecting changes in electron flow between two electrodes caused by absorption of the electrons by an electron capture gas flowing between said electrodes, means for supplying a carrier gas to said detecting means at a predetermined velocity, valve means for adding a sample of gas to said carrier gas at a first predetermined time, said sample gas containing a trace of a first type of electron capture gas, column means connected between said adding means and said detecting means for selectively slowing down the velocity of any other type of electron capture gas in said sample with respect to the velocity of the first type of electron capture gas, means coupled to said detector for measuring the maximum decrease in the electron flow caused by said first type of electron capture gas, and means coupled to said measuring means for indicating said maximum decrease, said measuring means including an integrating capacitor, a unidirectional device having one end thereof coupled to one end of said capacitor, a normally open switching means coupling a source of potential to said one end of said capacitor, amplifier means connecting one of said electrodes to the other end of said capacitor, said amplifier means and said unidirectional device being arranged so that decreases in electron flow in the detector reduces the charge on said capacitor, amplifying means for amplifying the voltage appearing across said capacitor, digital readout means coupled to said amplifying means, first timing means actuated by said valve means when said sample is added to said carrier gas and providing an output signal from its actuation until a time just prior to the arrival of the first type of electron capture gas between said electrodes, second timing means actuated by the termination of the output signal of said first timing means and providing an output signal from its actuation until a time just after the first type of electron capture gas passes beyond said electrodes, said normally open switch means being maintained closed except during the presence of said output signal of said second timing means, and means actuated by the termination of said output signal of said second timing means for holding the reading in said digital readout.

7. A gas monitor in accordance with claim 6 wherein said first type of gas is sulfur hexafluoride.

8. A gas monitor in accordance with claim 7 wherein said detecting means includes a tritium foil as a source of ionizing electrons.

9. A gas monitor in accordance with claim 8 wherein said column means is a molecular sieve column.

* * * * *